US005520623A

United States Patent [19]

Williams

[11] Patent Number: 5,520,623

[45] Date of Patent: May 28, 1996

[54] HEAD AND FACE SUPPORT DEVICE

[76] Inventor: Dallas Williams, 14920 Dilbeck Dr., Spring Hill, Fla. 34610

[21] Appl. No.: 399,519

[22] Filed: Mar. 7, 1995

[51] Int. Cl.[6] .......... A61F 5/00

[52] U.S. Cl. .......... 602/17; 602/18; 128/857; 2/9; 2/424; 5/637; 5/638

[58] Field of Search .......... 602/17, 18, 32, 602/35; 128/857, 869–870; 2/9, 424, 425; 5/637–638

[56] References Cited

U.S. PATENT DOCUMENTS 4,504,050 3/1985 Osborne .......... 5/637
4,823,776 4/1989 Foster et al. .......... 5/638 X
4,999,855 3/1991 Brown .......... 2/424 X
5,220,699 6/1993 Farris .......... 2/9 X
5,249,347 10/1993 Martinitz .......... 2/424 X
5,287,576 2/1994 Fraser .......... 5/637

*Primary Examiner*—Linda C. Dvorak
*Attorney, Agent, or Firm*—Stanley M. Miller

[57] ABSTRACT

A medical device immobilizes a patient's head and enables the patient to lie face down without turning the face to either side. A cushioned face-shaped frame has a rigid convex open mesh attached to it so that the patient's face is spaced apart from a support surface when the periphery of a patient's face lies against the cushioned frame. A transversely extending base having an adjustable height is connected to the frame by an interconnecting member having an adjustable length. The patient's chest overlies the base and therefore the face-receiving frame is held against movement when the device is in use. The effective height of the base and its distance from the frame are adjustable for the comfort of the patient.

5 Claims, 2 Drawing Sheets

HEAD AND FACE SUPPORT DEVICE

BACKGROUND OF THE INVENTION

1. Field of the Invention

This invention relates, generally, to devices having utility in the health care industry. More particularly, it relates to a device that enables a patient to lie face down without turning of the neck by supporting the patient's face about its periphery.

2. Description of the Prior Art

When a person is lying in the prone position, i.e., on the stomach, the head is normally turned to one side so that breathing is not inhibited by the pillow or other object that supports the head. However, a patient recovering from neck or back injury or surgery may not be able to comfortably turn his or her head to the side when lying on the stomach. This can cause a serious problem, especially if the patient cannot rest comfortably on his or her back.

Means are needed, therefore, that will enable a person whose head cannot be turned comfortably to lie on his or her stomach while awake or sleeping without inhibiting the breathing process.

Several pillow-like devices have been developed and patented that facilitate face down breathing. Such devices are disclosed in U.S. Pat. Nos. 5,095,569 to Glenn, 5,044,026 to Matthews, and 4,908,893 to Smit. Foreign patents disclosing special pillows include United Kingdom patent Nos. 1,048,632 and 1,199,533. A common shortcoming of all of these devices is that they do not stabilize the neck and head of the person using them. Thus, they may be suitable for use by uninjured people, but they cannot be relied upon by people with injured necks who require a stable support surface. More specifically, the earlier devices were designed to allow substantially unrestricted breathing of an uninjured individual sleeping in the prone position, but such devices were not designed to prevent the sleeping individual from moving his or her head and neck during sleep.

In view of the prior art as a whole at the time the present invention was made, it was not obvious to those of ordinary skill how the limitations of the prior art devices could be overcome.

SUMMARY OF THE INVENTION

The longstanding but heretofore unfulfilled need for a device that enables face down breathing when the head cannot be turned, and which supports the head in such a way that it will not turn, is now met. The device includes a face-receiving frame that is padded about its periphery to comfortably support the periphery of a patient's face, and a rigid, convex open mesh means is connected to the frame to space the patient's face above a support surface while permitting airflow so that the patient may breath without restriction.

A base member having an adjustable effective height is adjustably connected to the frame and is disposed beneath the patient's chest to hold the frame against movement when in use. But for the base, the frame would rock due to the convex shape of the open mesh means which overlies the support surface when the device is in use.

More particularly, the novel medical device includes a frame having a size and shape that substantially conforms to a human face and a rigid convex open mesh means attached to said frame. A cushioning means is disposed in overlying relation to said frame but not to said open mesh means so that the periphery of a persons's face may rest atop said cushioning means in the substantial absence of discomfort.

The novel device further includes a cushioned, transversely extending base of adjustable height, and an adjustable interconnecting means for interconnecting said frame and said base so that a person using said device overlies said base to hold the frame against movement, so that the convexity spaces the patient's face above the support surface upon which the device is positioned, so that airflow to the patient is not substantially restricted, and so that the patient's neck and head are immobilized by the device.

The primary object of this invention is to advance the art of health care by providing a device that enables neck or back patients to lie face down without turning their head and without restricting breathing.

A more specific object is to provide such a device in an inexpensive manner so that it is economical to manufacture and affordable to consumers.

Another very important object is to provide a head and neck supporting device that enables a patient with a neck injury to sleep through the night without fear of experiencing pain from neck movement.

These and other important objects, advantages, and features of the invention will become apparent as this description proceeds.

The invention accordingly comprises the features of construction, combination of elements, and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawing, in which.

DETAILED DESCRIPTION OF THE PREFERRED EMBODIMENT

Figure 1:
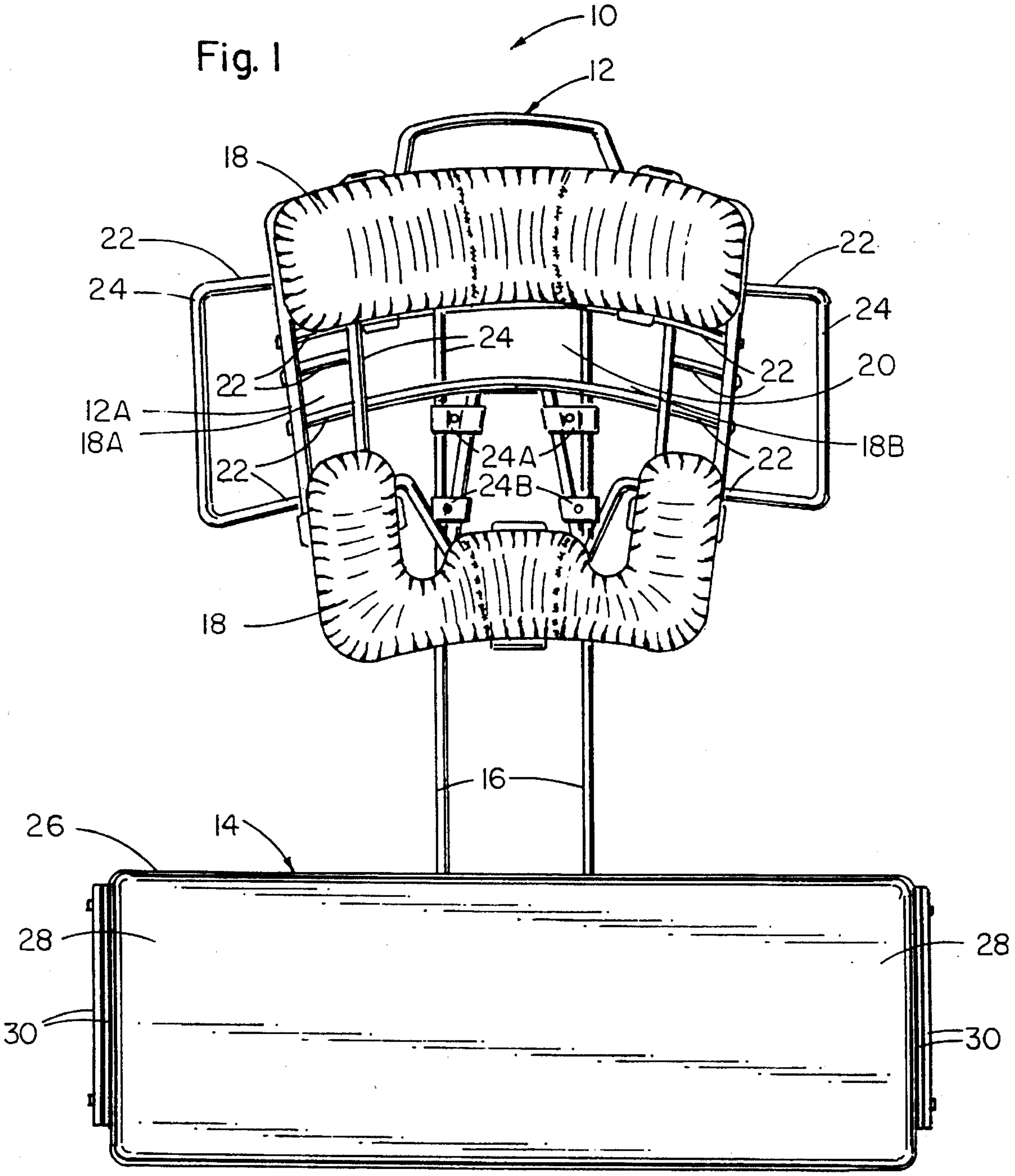
FIG. 1 is a perspective view of the top or inside of an exemplary embodiment of the invention.

Referring now to FIG. 1, it will there be seen that an illustrative embodiment of the invention is denoted as a whole by the reference numeral 10.

Support device 10, to be sold commercially under the trademark REST-EZ medical appliance, includes a frame 12, a base 14, and a slidable, adjustable interconnecting means 16 to provide spatial adjustment between frame 12 and base 14.

More specifically, frame 12 includes an oval or face-shaped metal or plastic frame 12A that is covered by a padding means 18 such as sponge material, foam rubber, or other suitable cushioning means. A rigid open mesh screen 20, also made of metal or plastic, is formed integrally with the frame and has a convex configuration as depicted in the Figure. Note that in this particular embodiment, there are five generally convex members, collectively denoted 22, that extend transversely and a plurality of longitudinally aligned, straight brace members, collectively denoted 24, that serve as brace means. Brace members 24 serve to enhance the structural integrity of the device.

Figure 3:
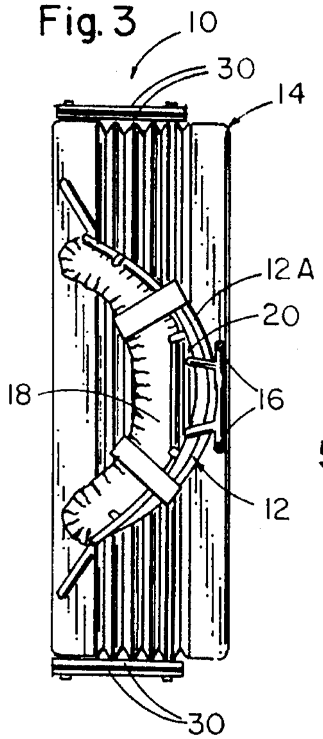
FIG. 3 is an end view thereof.
Figure 5:
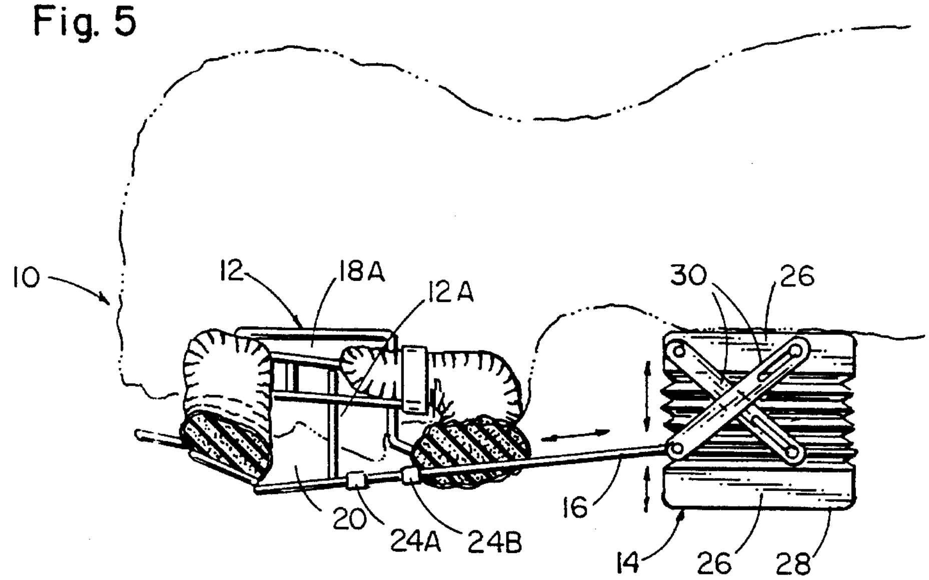
FIG. 5 is a sectional view taken along line 5—5 in FIG. 2.
Figure 4:
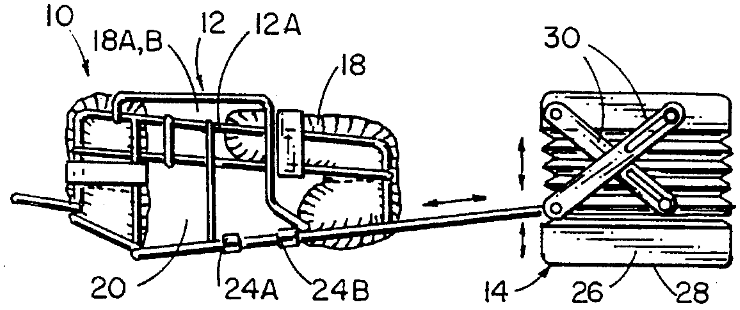
FIG. 4 is a side elevational view thereof.

Metal or plastic base 14 includes an inflatable accordion pleated bellows 26, as best understood in connection with FIGS. 3–5. The bellows include valves, not shown, so that they are orally inflatable in the well-known way. Pads 28, 28, provide padding for opposite sides of base 14.

A pair of generally diagonally disposed brace members, collectively denoted 30, are positioned at opposite sides of base 14; brace members 30 serve to stabilize the bellows 26 as the patient lies thereatop. Each brace has a first end that is pivotally secured to base 14 as depicted, and a slotted second end that receives a pin and which slides with respect thereto as the bellows expands and contracts, thereby increasing and decreasing the effective height of base 14, respectively. The bellows does not expand and contract after it has been inflated to a preselected inflation.

It should be understood that all mechanical means for adjusting the effective height of base 14 are within the scope of this invention, i.e., the bellows arrangement is one among many mechanical means for accomplishing the desired adjustment.

Figure 2:
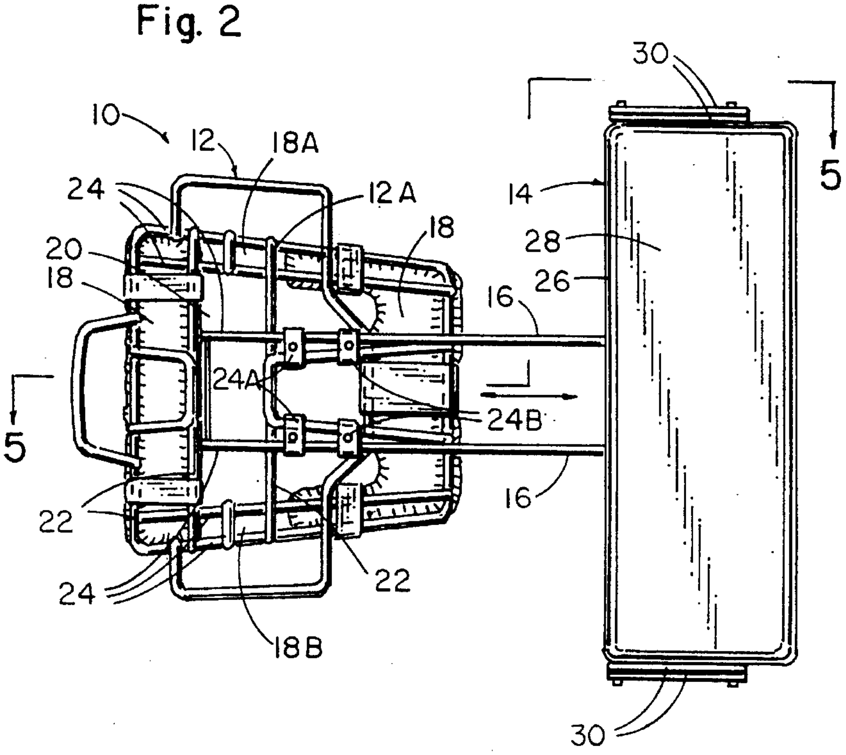
FIG. 2 is a bottom plan view thereof.

Connecting means 16 includes a pair of parallel, longitudinally aligned rods which are clamped as at 24A, 24B to two of the earlier-mentioned longitudinal brace members 24. The inboard part of each clamp securely grips the generally "U" shaped part of the frame as perhaps best understood in connection with FIG. 2, but the respective outboards parts thereof slidingly engage their associated longitudinal braces 24 so that the distance between the frame and base may be adjusted as indicated by the double-headed directional arrow in FIG. 2.

To use device 10, as best understood in connection with FIG. 5, the patient lies down with his or her face down and positioned within frame 12. The patient's chest overlies base 14 so that frame 12 cannot rock or otherwise move in any direction. The convexity of the open mesh 20 spaces the patient's face upwardly of the support surface upon which device 10 is positioned by a distance sufficient to not inhibit airflow to the patient, i.e., the curvature of open mesh 20 is sufficient to space the patient's nose above the support surface.

Interconnecting means 16 is also preferably formed of rigid material and, being adjustable as previously described, allows the patient to adjust the spacing between frame 12 and base 14 until the most comfortable spacing is found. Similarly, the effective height of base 14 is adjusted by inflation or deflation of the bellows until the most comfortable height of the base is determined.

The frame and other components may be constructed of any suitably rigid, preferably light-in-weight material and could take numerous other structural forms, all which are within the scope of this invention. Moreover, the REST-EZ medical device could be supplied in adult and pediatric sizes.

Note that facial support padding 18 is open at the sides thereof as at 18A and 18B to allow the patient's face to turn in either direction as well as straight down. Padding 18 does not interfere with the patient's nose during these variations in head positions.

A patient using this device may breath without restriction while in the prone position and sleep or rest without being disturbed by pain arising from head or neck movement. The weight of the patient's body immobilizes the device and the device immobilizes the patient's head and neck.

This invention is clearly new and useful. Moreover, it was not obvious to those of ordinary skill in this art at the time it was made.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A medical device, comprising:

a frame having a size and shape that substantially conforms to a human face;

a rigid convex open mesh means attached to said frame;

a cushioning means disposed in overlying relation to said frame so that a person's face may press thereagainst in the substantial absence of discomfort;

a transversely extending flat base covered by a second cushioning means;

an interconnecting means for interconnecting said frame and said base;

whereby a person using said device overlies said base to hold the frame against movement;

whereby said convexity spaces the patient's face above a support surface upon which the device is positioned so that airflow to the patient is not substantially restricted; and whereby the patient's neck and head are immobilized by said device.

2. A medical device, comprising:

a frame having a size and shape that substantially conforms to a human face;

a rigid convex open mesh means attached to said frame;

a cushioning means disposed in overlying relation to said frame so that a person's face may press thereagainst in the substantial absence of discomfort;

a transversely extending base;

an interconnecting means for interconnecting said frame and said base;

mechanical means for adjusting an effective height of said base;

whereby a person using said device overlies said base to hold the frame against movement;

whereby said convexity spaces the patient's face above a support surface upon which the device is positioned so that airflow to the patient is not substantially restricted; and whereby the patient's neck and head are immobilized by said device.

3. The device of claim 2, wherein said mechanical means includes an inflatable bellows.

4. A medical device, comprising:

a frame having a size and shape that substantially conforms to a human face;

a rigid convex open mesh means attached to said frame;

a cushioning means disposed in overlying relation to said frame so that a person's face may press thereagainst in the substantial absence of discomfort;

a transversely extending base;

an interconnecting means for interconnecting said frame and said base, said interconnecting means being adjustable in length so that a spacing between said frame and said base maybe adjusted for the comfort of the patient;

whereby a person using said device overlies said base to hold the frame against movement;

whereby said convexity spaces the patient's face above a support surface upon which the device is positioned so that airflow to the patient is not substantially restricted; and whereby the patient's neck and head are immobilized by said device.

5. The device of claim 4, wherein said interconnecting means includes a pair of straight, parallel interconnecting members.

* * * * *